United States Patent [19]
Ho et al.

[11] Patent Number: 5,023,171
[45] Date of Patent: Jun. 11, 1991

[54] METHOD FOR GENE SPLICING BY OVERLAP EXTENSION USING THE POLYMERASE CHAIN REACTION

[75] Inventors: Steffan N. Ho; Robert M. Horton, both of Rochester, Minn.

[73] Assignee: Mayo Foundation for Medical Education and Research, Rochester, Minn.

[21] Appl. No.: 392,095

[22] Filed: Aug. 10, 1989

[51] Int. Cl.$^5$ .............. C12Q 1/68; C07H 15/12; C12N 15/00

[52] U.S. Cl. .................................. 435/6; 536/27; 935/77; 935/78

[58] Field of Search .............. 435/6; 536/27; 935/77, 935/78

[56] References Cited
U.S. PATENT DOCUMENTS 4,683,202 7/1987 Mullis .............................. 435/91
4,800,159 1/1989 Mullis et al. ..................... 435/172.3

*Primary Examiner*—Robert A. Wax
*Assistant Examiner*—Mindy B Fleisher
*Attorney, Agent, or Firm*—Merchant, Gould, Smith, Edell, Welter & Schmidt

[57] ABSTRACT

A method is provided for joining two DNA molecules by first amplifying them by means of polymerase chain reactions (PCR) carried out on each molecule using oligonucleotide primers designed so that the ends of the resultant PCR products contain complementary sequences. When the two PCR products are mixed, denatured and reannealed, the single-stranded DNA strands having the complementary sequences at their 3' ends anneal and then act as primers for each other. Extension of the annealed area by DNA polymerase produces a double-stranded DNA molecule in which the original molecules are spliced together.

3 Claims, 4 Drawing Sheets

A. GENERATION OF FRAGMENTS

B. SOE REACTIONS

A: TEMPLATES

EXON 2 / INTRON 2

```
         Gly  Tyr  Tyr  Asn  Gln  Ser  Lys  Gly  G
7' -...GGC  TAC  TAC  AAC  CAG  AGC  AAG  GGC  G/GTGAGTGACCCCGG...-3'    H-2Kb
3' -...CCG  ATG  ATG  TTG  GTC  TCG  TTC  CCG  C/CACTCACTGGGGCC...-5'
       83   84   85   86   87   88   89   90
         Gly  Tyr  Tyr  Asn  Gln  Ser  Ala  Gly  G
5' -...GGC  TAC  TAC  AAC  CAG  AGC  GCG  GGC  G/GTGAGTGACCCCGC...-3'    H-2Ld
3' -...CCG  ATG  ATG  TTG  GTC  TCG  CGC  CCG  C/CACTCACTGGGGCG...-5'
```

INTRON 2 / EXON 3

```
                              ly   Ser  His  Thr  Ilu  Gln  Val  Ile
H-2Kb          5' -...CCCGCAG/GC  TCT  CAC  ACT  ATT  CAG  GTG  ATC...-3'
               3' -...GGGCGTC/CG  AGA  GTG  TGA  TAA  GTC  CAC  TAG...-5'
                                  91   92   93   94   95   96   97   98
                              ly   Ser  His  Thr  Leu  Gln  Trp  Met
H-2Ld          5' -...ACCGCAG/GC  ACT  CAC  ACA  CTC  CAG  TGG  ATG...-3'
               3' -...TGGCGTC/CG  TGA  GTG  TGT  GAG  GTC  ACC  TAC...-5'
```

B: PRIMERS

```
                          ← PRIMER "d"
         3'-cg  atg  atg  ttg  gtc  tcg  cgc  ccg  ccg  t-5'
                5'-ag  agc  gcg  ggc  ggc  act  cac  aca  ctc  cag-3'
                          PRIMER "e" →
```

C: PCR REACTIONS i)
```
5' -...GGC  TAC  TAC  AAC  CAG  AGC  AAG  GGC  G/GTGAGTGACCCCGG...-3'    H-2Kb
3' -...CCG  ATG  ATG  TTG  GTC  TCG  TTC  CCG  C/CACTCACTGGGGCC...-5'
       3'-cg  atg  atg  ttg  gtc  tcg  cgc  ccg  ccg  t-5'
                                    ← PRIMER "d"
``` ii)
```
                PRIMER "e" →
           5'-ag  agc  gcg  ggc  ggc  act  cac  aca  ctc  cag-3'
H-2Ld  5' -...ACCGCAG/GC  ACT  CAC  ACA  CTC  CAG  TGG  ATG...-3'
       3' -...TGGCGTC/CG  TGA  GTG  TGT  GAG  GTC  ACC  TAC...-5'
```

FIG. 3A

D: PCR PRODUCTS i)

FRAGMENT "AD"

5'—...GGC TAC TAC AAC CAG AGC GCG GGC GGC A-3'
3'—...Ccg atg atg ttg gtc tcg cgc ccg ccg t-5' ii)

5'—ag agc gcg ggc ggc act cac aca ctc cag TGG ATG...-3'
                3'—TC TCG CGC CCG CCG TGA GTG TGT GAG GTC ACC TAC...-5'
                                                                                              FRAGMENT "EH"

83   84   85   86   87   88   89   90   91   92   93   94   95   96   97   98
            Gly  Tyr  Tyr  Asn  Gln  Ser  Ala  Gly  Gly  Ser  His  Thr  Leu  Gln  Trp  Met
5'—...GGC TAC TAC AAC CAG AGC GCG GGC GGC ACT CAC ACA CTC CAG GTG ATG...-3'
3'—...CCG ATG ATG TTG GTC TCG CGC CCG CCG TGA GTG TGT GAG GTC CAC TAC...-5'

PRIMER "A": 5'-GCGTCCTCGGGTCGACCACCGGACCC-3'

PRIMER "C": 5'-GTTCGTGCGCTTCGACA-3'
PRIMER "B": 3'-AAGCACGCGAAGCTGTC-5'

PRIMER "G": 5'-CATCGCCCTGAACGAAG-3'
PRIMER "F": 3'-GTAGCGGGACTTGCTTC-5'

PRIMER "H": 3'-TCGGAAGAGGGAGCTCTCACGGGTCC-5'

FIG. 3B

METHOD FOR GENE SPLICING BY OVERLAP EXTENSION USING THE POLYMERASE CHAIN REACTION

BACKGROUND OF THE INVENTION

Standard methods for generating recombinant DNA constructs are sequence-dependent in that they rely on the use of restriction enzymes to cut DNA into specific fragments, which can then be rejoined in new combinations. Examples of engineered fusion proteins in the recent literature include: a ligand fused to a toxin to direct it to a specific cell type (Kim et al., 1988), a set of chimeric molecules used to map a determinant (Landau et al., 1988), and two peptide hormones fused to give a product with activities of both (Feng et al., 1988). Various engineering strategies were employed to generate these products, but each has its limitations. In one case, sequences from a multiple cloning site were used to join the two fragments, and the resultant protein thus contained irrelevant amino acids (Kim et al., 1988). In another example, silent restriction sites were introduced into the molecules to be recombined (Landau et al., 1988). This approach is limited by the requirement that the nucleic acid changes generating the restriction sites must not introduce undesired amino acid changes. In the third example, double-stranded synthetic oligos containing the desired fusion sequence were used to join the fragments (Feng et al., 1988). Even this approach, however, is dependent on the occurrence of restriction sites near enough to the fusion site to be included in a synthetic oligo.

SUMMARY OF THE INVENTION

The present invention, gene splicing by overlap extension (SOE), provides a new approach for recombining DNA molecules at precise junctions irrespective of nucleotide sequences at the recombination site and without the use of restriction endonucleases or ligase. Fragments from the genes that are to be recombined are generated in separate polymerase chain reactions (PCRs). The primers are designed so that the ends of the PCR products contain complementary sequences. When these PCR products are mixed, denatured and reannealed, the strands having the matching sequences at their 3' ends overlap and act as primers for each other. Extension of this overlap by DNA polymerase produces a molecule in which the original sequences are 'spliced' together. This technique is used to construct a gene encoding a mosaic fusion protein comprised of parts of two different mouse class-I major histocompatibility genes. This simple and widely applicable approach has significant advantages over standard recombinant DNA techniques. The construct produced encodes a chimeric protein in which the α-helices in one gene (the $L^d$ gene of the mouse class-I major histocompatibility complex) are replaced by the corresponding portions of a different gene from the same family ($K^b$). This construct will be used in future studies of structure-function relationships aimed at determining which portions of the molecule are important in antigen binding and T-cell recognition. The SOE approach is a fast, simple, and extremely powerful way of recombining and modifying nucleotide sequences.

BRIEF DESCRIPTION OF THE DRAWINGS

FIG. 3 shows the specific sequences at the joint between fragments AD and fragment EH, as well as the relevant primers and portions of intermediate products. (Part A) Comparison of the sequences of H-2$K^b$ and H-2$L^d$ at their exon 2/intron 2 and intron 2/exon 3 boundaries. Coding sequences are shown divided into codons with the corresponding amino acid indicated above. Numbers indicate the aa position in the class-I MHC molecule. A slash separates exons from introns, and dots indicate that the sequence extends beyond that shown. Primers 'd' and 'e', which hybridize to these regions, are depicted in part B in lower-case letters. Arrows indicate the direction in which each oligomer can act as a primer. (Part C): The primers aligned with their templates. (Part D): The ends of the resulting fragments AD and EH; sequences generated by DNA polymerase are shown in upper-case letters. The ends of these fragments share 15 homologous nt (Part E). The product of the SOE reaction between AD and EH, in which the top strand of AD and the bottom strand of EH overlap their 3' ends, and act as primers for one another. (Part F) Sequences of the other primers used in this project.

DETAILED DESCRIPTION OF THE INVENTION (a) General mechanism

Figure 1:
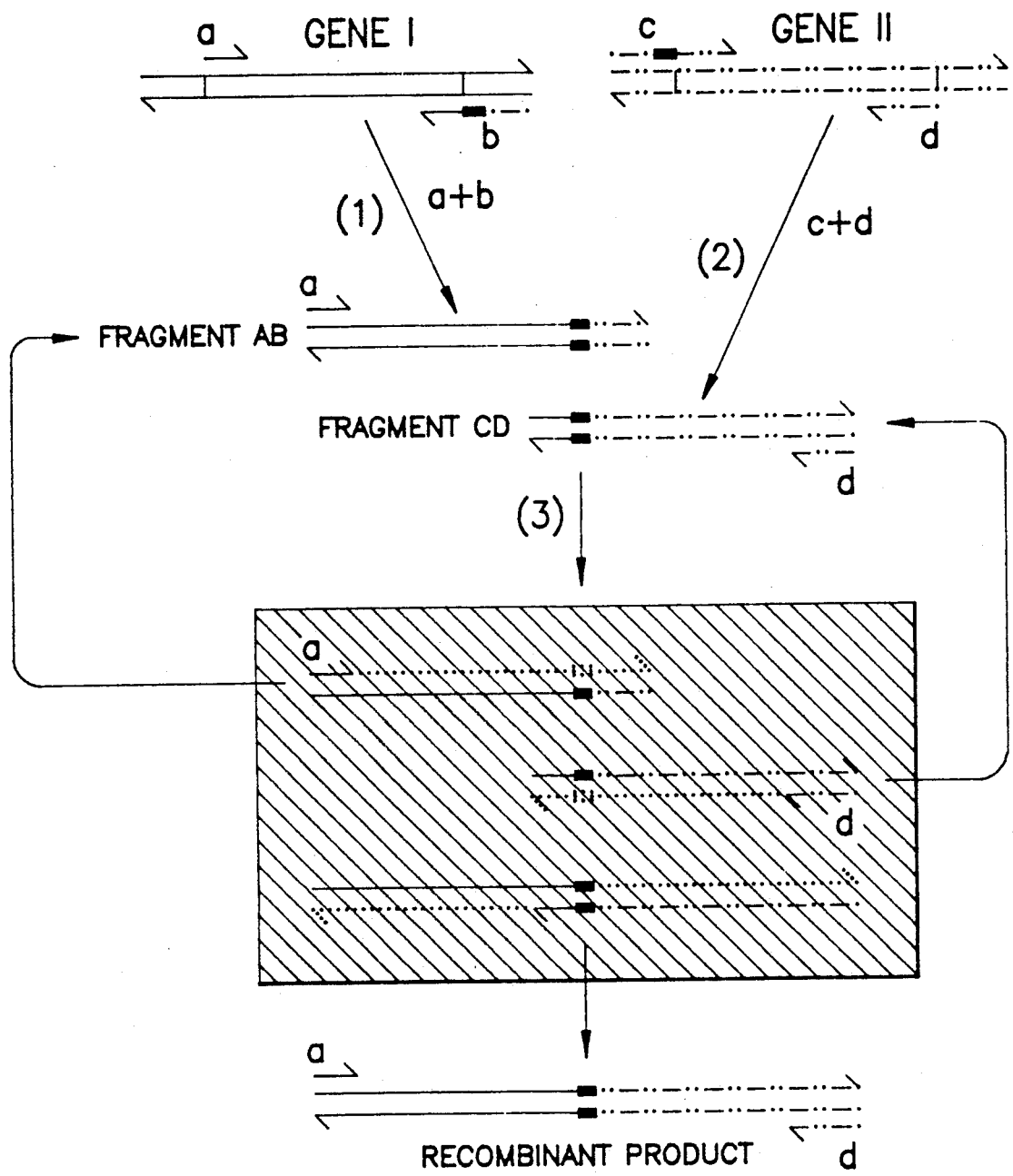
FIG. 1 schematically depicts the mechanism of gene splicing by overlap extension (SOE) in accord with the invention. Segments from two unrelated genes are to be spliced (DNA-I and DNA-II). Gene I is shown as solid lines and Gene II as dashes and dots. The 5'-3' direction of each strand is shown by half arrowheads. Oligos are labelled with single lower case letters, and PCR products are labelled using the two corresponding upper case letters; for example, reaction 1 is a PCR reaction using primers 'a' and 'b' (olig-a and olig-b) (on Gene I to generate the AB product (or DNA-A). Product CD (or DNA-B) is generated in a separate reaction by separating the strands of Gene II (DNA-II) to yield a second set of two single-stranded DNA molecules (DNA-3 and DNA-4) which are annealed with oligo-c and oligo-d, respectively, and amplified by PCR. Oligos 'b' and 'c' match their template genes in their 3' portions, but their 5' portions are designed so that the two oligos are complementary. The two PCR products are shown with the homologous segments aligned. In reaction (3), the segments are mixed along with excess primers 'a' and 'd', denatured, reannealed, and primer-extended by DNA polymerase (PCR conditions). The intermediates in this reaction are shown in the hatched box. The end of one strand from each product is capable of hybridizing with the complementary end from the other product. The strands having this overlap at their 3' ends can act as primers for one another and be extended by the polymerase to form the full-length recombinant product comprising a sequence corresponding to the sequences of the DNA-I and DNA-II linked by a sequence comprising DNA-b hybridized to DNA-c. DNA segments synthesized by the polymerase are shown as dotted lines. The recombinant product is PCR-amplified in the presence of 'a' and 'd'.

The general mechanism of SOE is illustrated in FIG. 1. The segments to be joined (fragment AB from Gene I and fragment CD from Gene II) are amplified in separate PCRs ('1' and '2'). The primers (or "oligos") used at the ends to be "SOEn" ('b' and 'c') are made complementary to one another by including nucleotides at their 5' ends that are complementary to the 3' portion of the other primer. This makes the PCR products of these first reactions overlap, that is, they share homologous sequences at the ends to be joined. These products are mixed in a SOE reaction (reaction 3) in which they are subjected to repeated rounds of denaturation, reannealing, and primer extension by DNA polymerase, in the PCR. The general methodology used for PCR is well known in the art, and is described in, e.g., C. Oste, *Biotechniques*, 6, 163 (1988) and K. B. Mullis (U.S. Pat. No. 4,683,202), the disclosures of which are incorporated by reference herein. One strand from each fragment contains the overlap sequence at the 3' end, and these strands can serve as primers for one another. Extension of this overlap by DNA polymerase yields the recombinant product. The other strands, which have the overlap at their 5' ends, are not capable of priming each other but they can act as templates for primers 'a' and 'd' and generate more of the original PCR products (AB and CD). The presence of the appropriate primers ('a' and 'd') in the reaction allows the recombinant product to be amplified by PCR as soon as it is formed.

The invention will be further described by reference to the following examples, where these abbreviations are used: aa, amino acid(s); ds, double-strand(ed); EtdBr, ethidium bromide; HLA, human leucocyte antigen(s); $K^b$, H-2$K^b$; kb, kilobase(s) or 1000 bp; $L^d$, H-2$L^d$; MHC, major histocompatibility complex; nt, nucleotide(s); oligo, oligodeoxyribonucleotide; PCR, polymerase chain reaction; SOE, splicing by overlap extension; "SOEn", spliced by overlap extension.

Example I (a) Materials and Methods

The $K^b$ gene was derived from a C57BL/6 genomic library (Schultz et al., 1983) and has been modified in our laboratory to include a SalI site in intron 1 and an XhoI site in intron 3. The $L^d$ gene was derived from a Balb/cJ genomic library (Moore et al., 1982). The sequence of $K^b$ from C57BL/10 (Weiss et al., 1983) and that of $L^d$ (Linsk et al., 1986) have been reported previously.

Oligos were made on an Applied Biosystems model 380A DNA synthesizer and desalted over a Sephadex G-50 column in distilled water. The PCR and the SOE reaction were carried out in an automated thermal cycler (PerkinElmer Cetus) for 25 cycles (each consisting of 1 min at 94° C., 2 min at 50° C., and 3 min at 72° C.), followed by a 10 min incubation at 72° C. One hundred pmol of each primer and 0.5 μl Taq polymerase (PerkinElmer Cetus) were used for each reaction in a volume of 100 μl using the reaction buffer recommended by the supplier.

DNA bands were recovered from agarose gels using GeneClean from Bio101. Sequencing of ds plasmid DNA was performed using a Sequenase kit from United States Biochemical Corporation, with a modified protocol (Kraft et al., 1988).

(b) Construction of recombinant molecule

Figure 2:
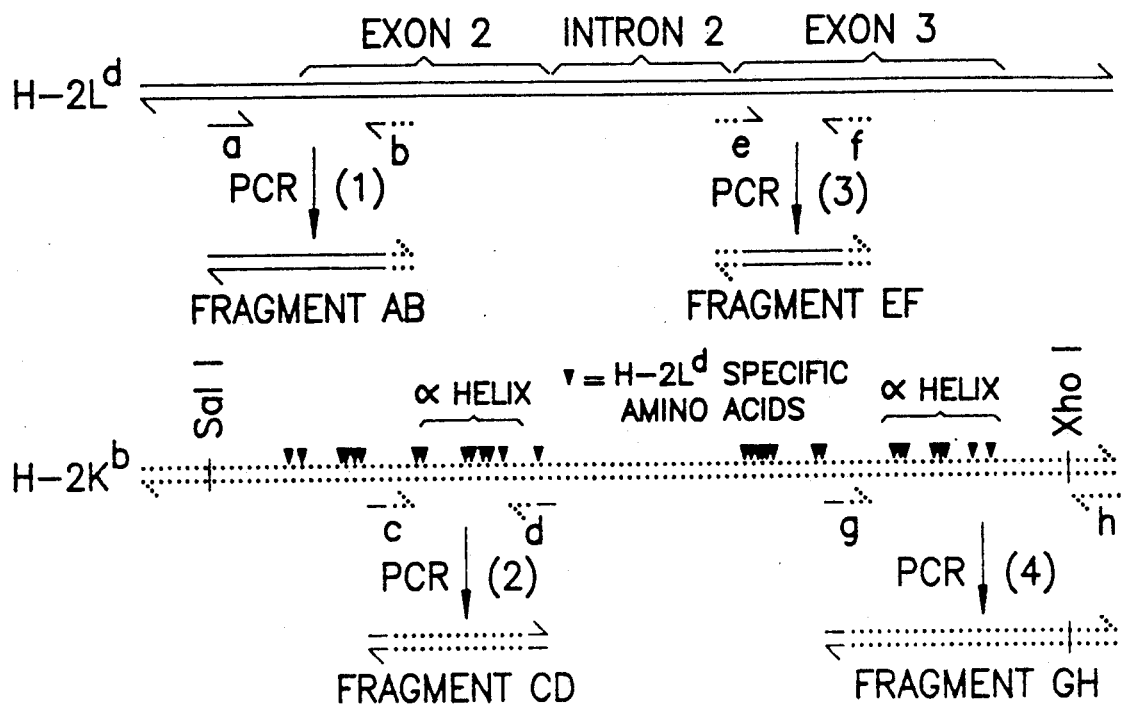
FIG. 2 schematically depicts one embodiment of the invention. Part A shows the two parental gene segments, the oligos used, and the fragments generated in the PCRs. Sequences originating from the $L^d$ gene are depicted as solid lines while those from $K^b$ are dotted lines. Small solid triangles indicate the positions of amino acids which are different in $K^b$ compared to $L^d$. The regions encoding α-helices and the positions of the relevant exons and intron are denoted by brackets. Fragment and oligo nomenclature is as in FIG. 1. AB and EF are generated from $L^d$ while CD and GH are generated from $K^b$. Part B shows the SOE reactions in which the gene fragments are recombined. This is done in three separate reactions: fragments AB and CD are combined to make AD, and EF and GH produce EH. The final reaction splices AD and EH to produce the recombinant molecule, AH, which has no intron 2. The recombinant product is cloned into the vector which originally contained the $K^b$ insert, using the SalI and XhoI sites.
Figure 2:
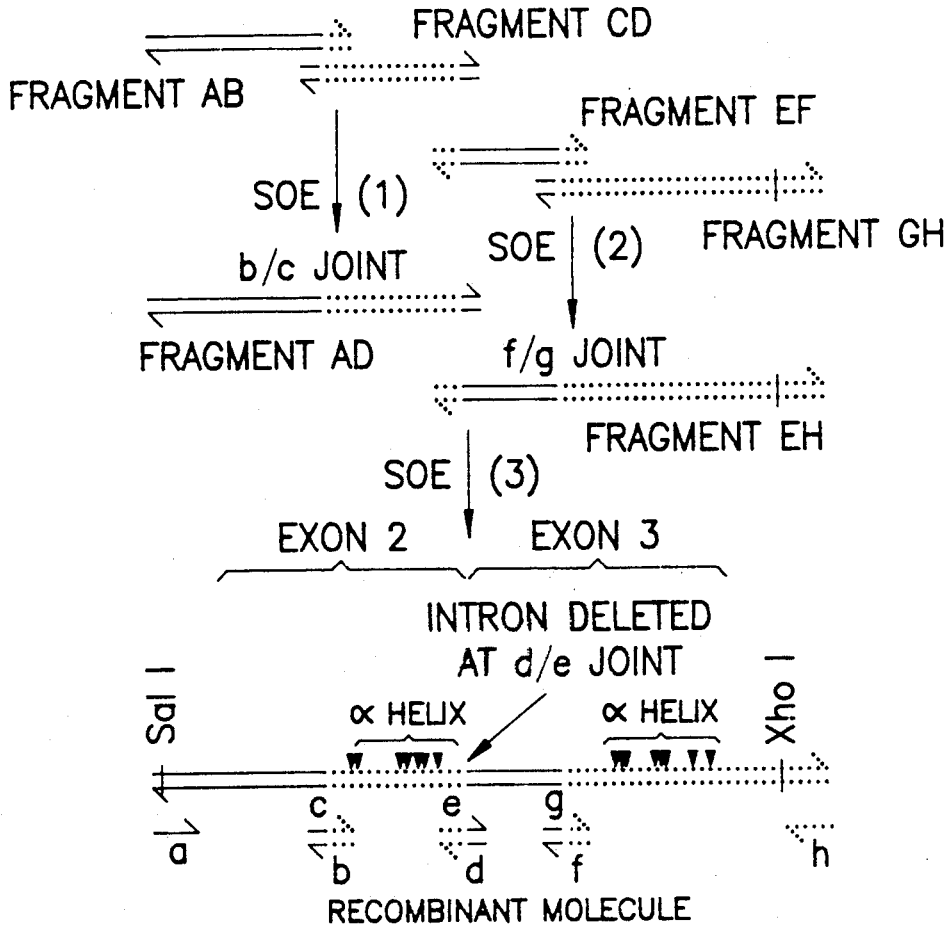

The design of the chimeric $K^b/L^d$ molecule is shown in FIG. 2. The positions of the α-helices indicated in the figure are inferred from the crystal structure of the human class-I MHC molecule HLA-A2 (Bjorkman et al., 1987). In the region encoded by exons 2 and 3, there are 30 specific aa differences between $L^d$ and $K^b$, denoted as inverted blackened triangles in the figure. Segments CD and GH which contain the α-helices, were PCR-amplified from $K^b$ and segments AB and EF, containing regions outside the helices, were amplified from $L^d$. Thus, the recombinant molecule made by SOEing these fragments together contains $K^b$ sequences in the α-helical regions.

As illustrated in reaction 1 of FIG. 2B, fragment AB is SOEd to fragment CD at the b/c joint, and in reaction 2, EF is "SOEn" to GH at the f/g joint. These joints are made using the least complex type of SOE oligomer pair in which the oligos are simply complementary to one another, as shown in FIG. 3E. The existence of regions of homology between the two proteins permitted some leeway in choosing the sites of the b/c and f/g joints. The joints were made in these conserved regions, rather than immediately at the ends of the α-helices, because suitable oligos had already been synthesized for other purposes.

The design of the oligomers for the d/e joint is more complicated. Exon 2 encodes aa 1-91, including the first α-helix. The α-helix ends at position 84, and there is a polymorphism between $L^d$ and $K^b$ at aa position 89. Therefore, a synthetic joint was needed to change the sequence from $K^b$ to $L^d$ near the end of exon 2. The following intron was deleted at the same time by splicing the sequence in exon 2 directly to sequences in exon 3. Details of the construction of this joint are given in FIG. 3. To delete the intron, the 'd' and 'e' oligomers could not simply contain complementary sequences of a conserved region, as was possible for the b/c and f/g joints described above. The 3' portion of oligomer 'd' hybridizes to the right side of exon 2 in the $K^b$ template, so that it can act as a primer for generation of fragment CD (which is subsequently "SOEn" to AB to generate AD). Similarly, the 3' end of oligomer 'e' allows it to act as a primer of the left side of exon 3 of $L^d$ to generate EF (and subsequently EH). Nucleotides in the 5' portion of primers 'd' and 'e' are designed to make them partially complementary to one another. This causes PCR products AD and EH to overlap at the d/e junction. Note that the d/e overlap encodes Ala, the $L^d$-specific aa at position 89. Thus, the AD/EH fusion product includes the sequence at the d/e junction that does not originate from either template (i.e., it is neither in exon 2 of $K^b$ nor in exon 3 of $L^d$). Rather, it is derived from the synthetic oligomers.

The products of the PCR and the SOE reaction described above were identified on an EtdBr-stained agarose gel. The four pieces were recovered from a similar gel using GeneClean, then assembling in two stages. In the first stage, AB and CD were "SOEn" together to yield AD; EF and GH were "SOEn" (in a separate reaction) to produce EH. In the second stage, these products were recovered from a gel and "SOEn" together to produce the recombinant product AH. The products are labeled as shown in FIG. 2. The expected sizes of the fragments are as follows: AB, 242 bp; CD, 178 bp; EF, 136 bp; GH, 463 bp; AD, 404 bp; EH, 582 bp; AH, 971 bp. Minor products are apparent in some lanes, most notably in EF, AD and EH but a band of the expected length is the major product in each reaction.

(c) Analysis of error frequency

The in vitro use of polymerase in PCR and SOE carries the potential for introducing random errors in the product. Theoretically, the probability of generating a random mutation with PCR and SOE reaction is significantly lowered by starting with large amounts of template, as this reduces the number of rounds of replication required to generate useful amounts of product and limits the opportunity for misincorporation of bases by the polymerase. Accordingly, 100 to 1000 ng of cloned template was used in the initial PCRs, and at least 25% of the recovered product from each step was used as reactant for the next step. The recombinant products were analyzed by cutting the AH product with the restriction enzymes SalI+XhoI and cloning into a pUC-derived vector. The nucleotide sequences of two independent clones of the recombinant molecule were determined. One of these clones was found to contain the entire correct sequence, while the other contained a single nucleotide substitution. This change in the mutant clone created a new PvuII site. To see whether this mutation was present in a large percentage of the recombinant molecules, DNA from nine more independent clones was isolated and cut with PvuII. None of these other clones contained the mutant site (not shown). Thus, of a total of approximately 1800 nt sequenced, we found one error, which is presumably due to misincorporation by the polymerase. This represents an error frequency of <0.06%.

In certain situations, the SOE method of recombining gene sequences is a significant improvement over standard techniques. It should prove particularly useful when sequences must be precisely joined within a very limited region as, for example, when inserting sequences into a vector of limited size, when changing the promoter of a gene without changing the start point of transcription or, as in the present case, when creating fusion proteins.

In addition to being an improved method for recombining DNA, SOE allows site-directed mutagenesis to be performed simultaneously with recombination. The product in a SOE reaction is a mosaic of natural sequences connected by synthetic regions, and the sequence of these synthetic regions is entirely at the discretion of the genetic engineer. This is the basis of the use of SOE for making insertions, deletions or changes within a sequence (Ho et al., 1989; Higuchi et al., 1988). In the present paper, the power of this approach is illustrated in reaction 3 of FIG. 2 and detailed in FIG. 3. Here, sequences from different exons are precisely joined and an amino acid is specifically changed, all in one step.

The following references, cited herein, are incorporated by reference herein:
P. J. Bjorkman et al., *Nature*, 329, 506 (1987).
G. Feng et al., *Science*, 241, 1501 (1988).
R. Higuchi et al., *Nucleic Acids Res.*, 16, 7351 (1988).
S. N. Ho et al., *Gene*, 77, 61 (1989).
J. Kim et al., *Gene*, 68, 315 (1988).
R. Kraft et al., *BioTechniques*, 6, 544 (1988).
N. R. Landau et al., *Nature*, 334, 159 (1988).
R. Linsk et al., *J. Exp. Med.*, 164, 794 (1986).
K. W. Moore et al., *Science*, 215, 679 (1982).
K. B. Mullis et al., *Methods Enzymol.*, 155, 335 (1987).
D. H. Schultz et al., *Mol. Cell. Biol.*, 3, 750 (1983).
E. Weiss et al., *EMBO J.*, 2, 453 (1983).

What is claimed is:

1. A method of forming a recombinant DNA molecule comprising:
   (a) separating the strands of a first double-stranded DNA molecule (DNA-I) to yield two single-stranded DNA molecules (DNA-1 and DNA-2);
   (b) annealing DNA-1 with a polyoligodeoxynucleotide primer (olgio-a) which is complementary to the 5'-end of DNA-1 and annealing DNA-2 with a second polyoligodeoxynucleotide primer (oligo-b) which is complementary to the 5'-end of DNA-2 and which further comprises a DNA sequence which extends beyond said 5'-end (DNA-b);
   (c) using the polymerase chain reaction (PCR) to synthesize an amount of DNA-I, designated DNA-A, which further comprises DNA-b and a DNA sequence complementary thereto;
   (d) separating the strands of a second double-stranded DNA molecule (DNA-II) to yield a second set of two single-stranded DNA molecules (DNA-3 and DNA-4);
   (e) annealing DNA-4 with a polyoligodeoxynucleotide primer (oligo-d) which is complementary to the 5'-end of DNA-4 and annealing DNA-3 with a polyoligodeoxynucelotide primer (oligo-c) which is complementary to the 5'-end of DNA-3 and which further comprises a DNA sequence which extends beyond said 5'-end of DNA-3 (DNA-c) and which is complementary to DNA-b;
   (f) using PCR to synthesize an amount of DNA-II, designated DNA-B, which further comprises DNA-c and a complementary DNA sequence corresponding to DNA-b;
   (g) combining and denaturing said portions of DNA-A and DNA-B, so that the strand of DNA-A comprising the DNA sequence complementary to DNA-b anneals to the strand of DNA-B comprising the DNA sequence corresponding to DNA-b at their 3'-ends to yield an annealed product; and
   (h) using DNA polymerase to synthesize a recombinant double-stranded DNA molecule from said annealed product, which comprises a sequence corresponding to the sequences of DNA-I and DNA-II linked by a sequence comprising DNA-b hybridized to DNA-c.

2. The method of claim 1 wherein the recombinant double-stranded DNA molecule of step (h) is amplified by the polymerase chain reaction in the presence of oligo-a and oligo-d.

3. The method of claim 1 wherein the DNA polymerase is Taq polymerase.

* * * * *

UNITED STATES PATENT AND TRADEMARK OFFICE
CERTIFICATE OF CORRECTION

PATENT NO. : 5,023,171

DATED : June 11, 1991

INVENTOR(S) : Ho et al.

It is certified that error appears in the above-identified patent and that said Letters Patent is hereby corrected as shown below:

At column 2, line 8, for "(olig-a and olig-b)" read --(oligo-a and oligo-b)--.

At column 2, line 8, for "(on" read --on--.

At column 2, line 30, after "of" delete --the--.

In claim 1, at column 6, line 22, for "(olgio-a)" read --(oligo-a)--.

Signed and Sealed this

Twelfth Day of January, 1993

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO.    : 5,023,171
DATED         : June 11, 1991
INVENTOR(S)   : Steffan N. Ho and Robert M. Horton It is certified that error appears in the above-identified patent and that said Letters Patent is hereby corrected as shown below:

Column 6,
Lines 21 and 23, please delete "DNA-1" and insert -- DNA-2 -- therefor.
Lines 23, 25, 27, 38, 40 and 42, please delete "5'-end" and insert -- 3'-end -- therefor.
Lines 23 and 25, please delete "DNA-2" and insert -- DNA-1 -- therefor.
Lines 36 and 38, please delete "DNA-4" and insert -- DNA-3 -- therefor.
Lines 38, 40 and 42, please delete "DNA-3" and insert -- DNA-4 -- therefor.

Signed and Sealed this

Twenty-ninth Day of June, 2004

JON W. DUDAS
*Acting Director of the United States Patent and Trademark Office*